United States Patent [19]

Blum et al.

[11] Patent Number: 4,719,050

[45] Date of Patent: Jan. 12, 1988

[54] DIPHOSPONYLATED OXONITRILES, PROCESSES AND USES THEREFOR, AND COMPOSITIONS CONTAINING THEM

[75] Inventors: Helmut Blum, Duesseldorf; Siglinde Hemmann, Meerbusch, both of Fed. Rep. of Germany

[73] Assignee: Henkel Kommanditgesellschaft auf Aktien, Duesseldorf, Fed. Rep. of Germany

[21] Appl. No.: 26,098

[22] Filed: Mar. 16, 1987

[30] Foreign Application Priority Data

Apr. 5, 1986 [DE] Fed. Rep. of Germany ....... 3611522

[51] Int. Cl.$^4$ ............................ C07F 9/38; A61K 7/16; A61K 7/48
[52] U.S. Cl. ......................... 260/502.5 C; 260/501.12; 424/49; 514/76; 514/108
[58] Field of Search ...................... 260/502.5 C, 501.12

[56] References Cited

U.S. PATENT DOCUMENTS

| | | | |
|---|---|---|---|
| 3,899,496 | 8/1975 | Schindler et al. | 260/502.5 C |
| 4,006,182 | 2/1977 | Ploger et al. | 260/502.5 C |
| 4,239,695 | 12/1980 | Chai et al. | 260/502.5 C |

FOREIGN PATENT DOCUMENTS

| | | | |
|---|---|---|---|
| 0054195 | 6/1982 | European Pat. Off. | 260/502.5 C |
| 1002355 | 2/1957 | Fed. Rep. of Germany | 260/502.5 C |
| 1958123 | 5/1971 | Fed. Rep. of Germany | 260/502.5 C |
| 2625767 | 12/1977 | Fed. Rep. of Germany | . |
| 1508772 | 4/1978 | United Kingdom | 260/502.5 C |

*Primary Examiner*—J. E. Evans

*Attorney, Agent, or Firm*—Ernest G. Szoke; Henry E. Millson, Jr.

[57] ABSTRACT

3-Alkyl-3-oxo-1-aminopropane-1,1-diphosphonic acids and water-soluble salts thereof corresponding to the formula

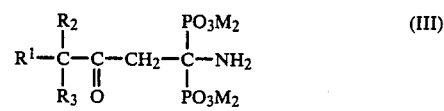

in which $R^1$ represents an unbranched or branched $C_1$-$C_8$ alkyl group, $R^2$ and $R^3$ independently of one another represent methyl or ethyl, and each M represents H or a cation of a water-soluble base, to a process for producing these compounds wherein oxonitriles corresponding to the formula:

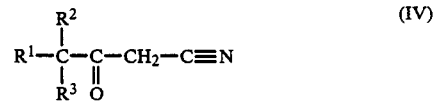

in which $R^1$, $R^2$ and $R^3$ are as defined above, are reacted with mixtures of a phosphorus trihalide $PX_3$, where X represents fluorine, chlorine or bromine, with phosphorous acid, the reaction mixture is hydrolyzed, and the reaction products are optionally converted into water-soluble salts; and to the use of the resulting compounds corresponding to general formula (III).

5 Claims, No Drawings

DIPHOSPONYLATED OXONITRILES, PROCESSES AND USES THEREFOR, AND COMPOSITIONS CONTAINING THEM

BACKGROUND OF THE INVENTION

1. Field of the Invention

This invention relates to 3-alkyl-3-oxo-1-aminopropane-1,1-diphosphonic acids obtainable by diphosphonylation of oxonitriles, to water-soluble salts thereof, to a process for their production, to their use as microbistatic agents, and to microbistatic compositions containing them.

2. Statement of Related Art

1-Amino-1,1-diphosphonic acids corresponding to the following general formula

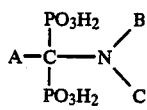

in which A, B and C represent a liphatic, cycloaliphatic or aromatic hydrocarbon radicals, in addition to which B and C may additionally represent a hydrogen atom, are known from the prior art. They are prepared by reaction of nitriles with phosphorus trihalides and subsequent hydrolysis or alcoholysis (German Application No. 10 02 355), by reaction of nitriles with phosphorous acid (German Application No. 26 25 767), or by reaction of carboxylic acid amides with phosphorus trihalides in the presence of phosphorous acid and subsequent hydrolysis (German Application No. 19 58 123). Phosphonic acids corresponding to general formula (I) above are capable of complexing heavy-metal ions and alkaline-earth metal ions. Accordingly, they are widely used as complexing agents and chelating agents for softening water, in the manufacture of detergents in the textile field and in paper making. In addition, German Application No. 10 02 355 mentions their use in pharmaceuticals and pesticides.

In addition, structurally related compounds corresponding to the following general formula

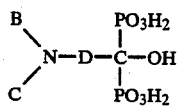

which are also known as complexing agents, are known to be useful in the pharmaceutical field. In formula (II), B and C represent hydrogen or aliphatic or aromatic radicals in accordance with general formula (I) above while D is a $C_1$–$C_5$ alkylene radical. German Patent Nos. 24 05 254 and 25 34 391 describe the use of compounds corresponding to general formula (II) and water-soluble salts thereof in the prophylaxis and therapeutic treatment of disorders of the calcium or phosphate metabolism in humans and animals.

STATEMENT OF THE INVENTION

Other than in the operating examples, or where otherwise indicated, all numbers expressing quantities of ingredients or reaction conditions used herein are to be understood as modified in all instances by the term "about".

It has now surprisingly been found that new compounds can be obtained by phosphonylation of oxonitriles and that these compounds exhibit very good microbistatic properties. Accordingly, they can be used as an active component in compositions for inhibiting the growth of microorganisms.

The present invention relates to 3-alkyl-3-oxo-1-aminopropane-1,1-diphosphonic acids and water-soluble salts thereof corresponding to the following general formula

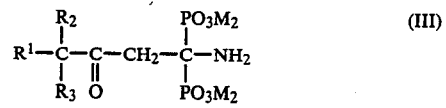

in which $R^1$ represents an unbranched or branched $C_1$–$C_8$ alkyl group, $R^2$ and $R^3$ independently of one another represent methyl or ethyl and M can be H or the cation of a water-soluble base.

The invention also relates to a process for preparing the compounds corresponding to general formula (III) by reacting an oxonitrile corresponding to the following general formula

in which $R^1$, $R^2$ and $R^3$ have the meanings defined above, at 0° to 100° C., optionally in the presence of one or more organic solvents, either with (a) a mixture of phosphorus trihalide ($PX_3$, in which X represents F, Cl or Br) and phosphorous acid (wherein the molar ratio of the phosphonylation reactants are from 2:1 to 1:2), or (b) products of the reaction of phosphorus trihalides ($PX_3$) with water in which the phosphorus trihalide is hydrolyzed to such an extent that a $PX_3/H_3PO_3$ mixture in a molar ratio of from 2:1 to 1:2 is present. An excess of water is added to the above reaction mixture. The resulting reaction products which correspond to general formula (III) in which all M groups represent H, are then optionally converted into compounds corresponding to formula (III) in which all or a portion of the M groups are alkali metal or ammonium cations, by addition of basic reactants corresponding to the formula $M^\oplus OH^\ominus$ where $M^\oplus$ is an alkali metal or ammonium cation $R^4R^5R^6R^7N^\oplus$, in which $R^4$, $R^5$, $R^6$ and $R^7$ independently of one another represent hydrogen or a branched or unbranched $C_1$–$C_{12}$ alkyl group. The resulting compounds corresponding to formula (III) are isolated and purified using conventional purification techniques.

The invention also relates to compositions containing one or more of the compounds corresponding to general formula (III) in microbistatically active concentrations in addition to standard carriers and auxiliaries, and the use of such compositions as microbistatic agents.

The new compounds of general formula (III) may be termed 3-alkyl-3-oxo-1-aminopropane-1,1-diphosphonic acids or salts thereof, depending on the substituents $R^1$, $R^2$, $R^3$ and M. In general formula (III), $R^1$ represents an unbranched or branched $C_1$–$C_8$ alkyl group, e.g. methyl, ethyl, n-propyl, l-propyl, n-butyl, sec.-butyl, tert.-butyl, and also n-pentyl, n-hexyl, n-heptyl, n-octyl and branched isomers of the foregoing. $R^1$ preferably represents an unbranched alkyl group containing from 3 to 6 C-atoms.

The substituents $R^2$ and $R^3$ in general formula (III) above independently of one another represent methyl or ethyl. The two substituents $R^2$ and $R^3$ are preferably the same. Compounds (III) according to the invention in which both substituents $R^2$ and $R^3$ represent methyl are particularly preferred.

Compounds corresponding to general formula (III) above, in which M—instead of the proton for the free acids—represents alkali metal cations or ammonium cations corresponding to the general formula $R^4R^5R^6R^7N^\oplus$, also show microbistatic activity and, accordingly, fall within the scope of the invention. A major advantage of these salts derived from the free acids is that they distinctly improve the solubility in water of the compounds corresponding to general formula (III) in which all M groups represent H. Naturally, this also makes the compounds in question easier to use in microbistatic preparations. According to the invention, cations such as $Na^+$ or $K^+$ are particularly suitable alkali metal cations. However, M can also represent ammonium cations corresponding to the above general formula, in which $R^4$, $R^5$, $R^6$, and $R^7$ independently of one another may represent hydrogen or branched or unbranched $C_1$–$C_{12}$ alkyl groups. Suitable alkyl groups are any branched and unbranched groups from the following: methyl, ethyl, propyl, butyl, pentyl, hexyl, heptyl, octyl, nonyl, decyl, undecyl and dodecyl.

According to the invention, preferred water-soluble salts are alkali metal salts corresponding to general formula (III), in which all M groups represent an alkali metal cation. The sodium salts are particularly preferred.

According to the invention, the compounds corresponding to general formula (III) are prepared by phosphonylation of oxonitriles corresponding to the following general formula

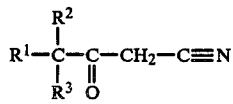

(IV)

in which $R^1$, $R^2$ and $R^3$ have the meanings given above, with mixtures of phosphorus trihalides $PX_3$ (where X=F, Cl, or Br) with phosphorous acid, the molar ratio of the phosphonylation reactants being from 2:1 to 1:2, but preferably 1:1. $PBr_3$ is advantageously used as the phosphorus trihalide in the process of the invention. A similar reaction is described in German Application No. 19 58 123.

Instead of using a mixture of phosphorus trihalide and phosphorous acid, it is also possible to use a reaction product of phosphorus trihalide with water where the quantities formed during the reaction are such that a mixture of phosphorus trihalide and phosphorous acid in a molar ratio of, for example, 1:1 is present. This may be achieved, for example, by using mixtures of phosphorus trihalide, for example phosphorus tribromide, and water in a molar ratio of 2:3 in which 1 mole $PX_3$ is hydrolyzed to phosphorous acid while the other is available for phosphonylation of the oxonitrile (IV).

The phosphonylation reaction can be carried out in the presence of absence of one or more organic solvents, such as dioxane, chlorobenzene, glycol dimethylether, halogenated hydrocarbons, such as carbon tetrachloride or ethane tetrachloride, etc. The reaction temperatures are preferably in the range of from 0° to 100° C. and more preferably in the range of from 45° to 90° C. In general, the reaction is carried out by successively or simultaneously introducing the phosphorous acid and the phosphorus trihalide or by successively introducing phosphorus trihalide and water into the oxonitrile corresponding to general formula (IV) in one of the organic solvents mentioned above. The reaction mixture is stirred for a period, for example for 3 to 7 hours, in the temperature range indicated. It is then hydrolyzed with an excess of water.

The resulting reaction products corresponding to general formula (III), in which M represents H, are then optionally converted into their water-soluble salts, preferably their alkali metal salts and more preferably their sodium salts by addition of basic reagents corresponding to the formula $M^\oplus OH^\ominus$, where $M^\oplus$ is an alkali metal or ammonium cation, and isolated from the reaction mixture and purified by known methods. This may be done, for example, by crystallizing out the reaction products dissolved in the reaction mixture at elevated temperature by cooling or precipitating them by addition of a solvent, separating the resulting precipitates or crystals from the dissolved reactants by decantation of the mother liquor or by filtration and then drying the precipitates or crystals and, optionally, further purifying them by recrystallization.

In addition, it has surprisingly been found that the above-mentioned compounds corresponding to general formula (III) show excellent microbistatic activity against numerous bacteria. Accordingly, they can be used with advantage in microbistatic preparations. To this end, one or more compounds corresponding to general formula (III) are formulated, preferably in quantities of from 0.1 to 1 g/l, with standard carriers and auxiliaries to form microbistatic compositions. Particularly favorable activity was shown by compositions containing one or more compounds corresponding to general formula (III), in which $R^3$ is a straight-chain or branched $C_3$–$C_6$ alkyl group, $R^2$ and $R^3$ represent methyl and all M groups are alkali metal cations, preferably sodium ions, in concentrations of from 0.25 to 1 g/l together with standard carriers and auxiliaries.

Compositions such as these are particularly suitable for inhibiting the growth of numerous gram-positive and gram-negative bacteria, even in low concentrations. In this connection, they have an inhibiting concentration which makes them distinctly superior to other comparable microbistatic compositions. These compositions are useful in the treatment of hard surfaces to prevent or minimize growth of microoganisms, e.g. in the cleaning and treatment of floors and walls in hospitals, food processing plants, and other private and public buildings.

In addition, the compounds of the invention can be employed to inhibit the growth of gram-positive and gram-negative bacteria in the oral cavity, for example, as a component of disinfectant toothpastes and mouthwashes, present in the quantities given above. They can also be employed in compositions used in disinfecting mammalian skin surfaces, e.g. in aqueous or ethanol-based disinfectant solutions. They can also be employed as a microbistatic agent in cosmetic compositions, for example to preserve cosmetic salves, creams and lotions, which are otherwise subject to bacterial contamination.

The invention is illustrated but not limited by the following Examples.

EXAMPLE 1

0.2 mole 4,4-dimethyl-3-oxoheptanoic acid nitrile (IV, $R^2=R^3=CH_3$, $R^1=n-C_3H_7$) were dissolved in 150 ml dioxane while heating to 40° C., followed by the introduction of 0.2 mole phosphorous acid. 0.6 mole $PBr_3$ was then slowly added dropwise and, after heating to 80° C., the reaction mixture was stirred for 5 hr. at that temperature. The reaction mixture was then hydrolyzed with 1.8 moles water at the same temperature. After 1 hr. another 80 ml water were added, followed by brief boiling and cooling. The deposit precipitated was repeatedly washed with water and then with acetone and dried in vacuo at 60° C. 24.3 g (38.3% of the theoretical) of 1-amino-4,4-dimethyl-3-oxo-heptane-1,1-diphosphonic acid ((III), $R^1=n-C_3H_7$, $R^2=R^3=CH_3$, $M=H$) were isolated in this way.

Mp.: 176° C. (decomp.)

Elemental analysis (%): Calculated: C 34.07; H 6.62; N 4.42; P 19.56. Found: C 34.65; H 6.90; N 4.50; P 19.80.

EXAMPLE 2

0.2 mole 4,4-dimethyl-3-oxodecanoic acid nitrile ((IV), $R^1=n-C_6H_{13}$, $R^2=R^3=CH_3$) was reacted with phosphorous acid and $PBr_3$ as in Example 1. To complete the reaction, the reaction mixture was stirred for 7 hr., yellow-orange colored decomposition products being formed. To separate off these decomposition products, the hydrolyzate was alkalized, filtered and the phosphonic acid product precipitated by acidification to a pH value of 1 with hydrochloric acid. 25.2 g (35.1% of the theoretical) of 1-amino-4,4-dimethyl-3-oxodecane-1,1-diphosphonic acid ((III), $R^1=n-C_6H_{13}$, $R^2=R^3=CH_3$; $M=H$) were obtained in this way.

Mp.: 173° C. (decomp.)

Elemental alaiysis (%): Calculated: C 40.11; H 7.52; N 3.90; P 17.27. Found: C 40.90; H 7.75; N 3.83; P 17.00.

EXAMPLE 3

The compounds of Examples 1 and 2 were tested for their microbistatic activity.

For testing the compounds of general formula (III) according to the invention, a so-called "liquid inhibition series" was prepared. The microbistatic activity was tested against the following test bacteria:

(1) *Staphylococcus aureus;*
(2) *E. coli;*
(3) *Pseudomonas aeruginosa;*
(4) *Streptococcus mutans.*

An overnight culture of the test bacteria was prepared one day before preparation of the actual test series. To this end, a little bacterial mass was removed with an inoculation loop from a densely bacteria-populated part of the plate and introduced into a test tube filled with 10 ml bouillon. The corresponding test tubes were then incubated for 16-18 hr. at 37° C. and subsequently stored at 4° to 0° C. pending inoculation of the test tubes.

The test compounds of Examples 1 and 2 were weighed in the following amounts into sterile Erlenmeyer flasks:

(a) 0.02 g to 3 ml solvent (see below) corresponding to 5000 ppm and
(b) 0.10 g to 2 ml solvent corresponding to 50,000 ppm.

The solid samples were then dissolved in 4 ml and 2 ml of the solvent (demineralized water or corresponding organic solvent). Solutions containing 5000 ppm and 50,000 ppm were thus obtained (see above).

Using an automatic pipette, the solutions prepared as described above were transferred in the following volumes to sterile test tubes filled with 5 ml bouillon or broth, producing the concentration of microbistatic agent indicated below for 5 ml bouillon or broth:

Of solution (a):
10 μl, corresponding to a concentration of 10 ppm;
50 μl, corresponding to a concentration of 50 ppm and
100 μl, corresponding to a concentration of 100 ppm.

Of solution (b):
25 μl, corresponding to a concentration of 250 ppm;
50 μl, corresponding to a concentration of 500 ppm and
100 μl, corresponding to a concentration of 1000 ppm.

Dilution series such as these were prepared for both compounds (Example 1 and Example 2). The corresponding test tubes were then shaken to guarantee thorough intermixing.

To determine the microbistatic activity of the compounds (III), the test tubes were each inoculated with one drop of the corresponding bacteria suspension. A test tube filled with 5 ml bouillon or broth, but with no bacteria added, was used as growth control for all the test bacteria. The corresponding test tubes were incubated for 48 hr. at 37° C.

The result was evaluated by reading off in the dilution series the dilution stage at which the compound to be tested for microbistatic activity inhibited the growth of the test bacteria, i.e. the dilution stage at which the bouillon or broth remained clear.

The following Table shows the microbistatic activity of the compounds of Examples 1 and 2 against gram-positive test bacteria (Staphylococcus aureus and Streptococcus mutans) and gram-negative test bacteria (Pseudomonas aeruginosa and Escherischia coli). In the Table, the inhibiting concentrations are given in ppm.

TABLE

| Compound of Example No. | Inhibiting concentrations (ppm) for | | | |
|---|---|---|---|---|
| | Staph. aureus | Strept. mutans | Pseud. aerugin. | E. coli |
| 1 | 500 | 1000 | — | 1000 |
| 2 | 250 | 250 | 1000 | — |

We claim:

1. A 3-alkyl-3-oxo-1-aminopropane-1,1-diphosphonic acid or water-soluble salt thereof of the formula $$R^1-\underset{\underset{R_3}{|}}{\overset{\overset{R_2}{|}}{C}}-\underset{\underset{O}{\|}}{C}-CH_2-\underset{\underset{PO_3M_2}{|}}{\overset{\overset{PO_3M_2}{|}}{C}}-NH_2 \quad (III)$$

in which $R^1$ represents an unbranched or branched $C_1-C_8$ alkyl group, $R^2$ and $R^3$ independently of one another represent methyl or ethyl, and each M can be H or a cation of a water-soluble base.

2. A compound of claim 1 wherein $R^1$ represents an unbranched $C_3-C_6$ alkyl group.

3. A compound of claim 1 wherein $R^2$ and $R^3$ both represent methyl.

4. A compound of claim 2 wherein $R^2$ and $R^3$ both represent methyl.

5. A compound of claim 1 wherein each m is an alkali metal cation or an ammonium cation corresponding to the formula $R^4R^5R^6R^7N^+$, in which $R^4$, $R^5$, $R^6$ and $R^7$ independently of one another represent hydrogen or an unbranched or branched $C_1-C_{12}$ alkyl group.

* * * * *